(12) United States Patent
Hasegawa et al.

(10) Patent No.: US 6,169,174 B1
(45) Date of Patent: Jan. 2, 2001

(54) COTTON PLANT GENE

(75) Inventors: Osamu Hasegawa; Satoshi Aotsuka; Soichiro Takenishi, all of Tokyo; Hirofumi Uchimiya, Kawasaki, all of (JP)

(73) Assignee: Nisshinbo Industries, Inc., Tokyo (JP)

( * ) Notice: Under 35 U.S.C. 154(b), the term of this patent shall be extended for 0 days.

(21) Appl. No.: 08/934,627

(22) Filed: Sep. 19, 1997

(30) Foreign Application Priority Data

Sep. 20, 1996 (JP) .................................................. 8-250122

(51) Int. Cl.[7] .............................. C07H 21/04; C12Q 3/00; C07K 1/00
(52) U.S. Cl. .............................. 536/23.6; 435/6; 530/350; 530/370
(58) Field of Search .................................... 530/350, 370; 435/6; 536/23.6

(56) References Cited

U.S. PATENT DOCUMENTS 5,521,078  5/1996  John .................................. 435/172.3

FOREIGN PATENT DOCUMENTS

| 0 707 065 A2 * | 4/1996 | (EP) . |
| WO 93 15213 | 8/1993 | (WO) . |
| WO 96 34088 | 3/1996 | (WO) . |

OTHER PUBLICATIONS

GenBank Accession X64392, submitted by Baltz et al., publicly available on Apr. 21, 1993.*
GenBank Accession T29008, submitted by Mohapatra et al., publicly available on Sep. 16, 1996.*
Baltz, R., et al., "Characterization of a pollen–specific cDNA from sunflower encloding a zinc finger protein" The Plant Journal, vol. 2, No. 5, 1992, pp. 713–721.
Newman, T., et al.; "5470 Lambda–PRL2 Arabidopsis thaliana cDNA clone 111C13T7", EMBL Accession No. T42207, Feb. 2, 1995.
Michael, A. J., et al. Isolation by PCR of a CDNA Clone from pea petals with Similarity to Petunia and wheat zinc finger protein; Plant Molecular Biology, vol. 30, Mar. 1996.
John, M. E.: Structural characterization of genes corresponding to cotton fiber mRNA, E6; reduced E6 protein in transgenic plants by antisense gene; Plant Molecular Biology, vol. 30, Jan. 1996, pp. 297–306.

* cited by examiner

Primary Examiner—Ponnathapu Achutamurthy
Assistant Examiner—Bradley S. Mayhew
(74) Attorney, Agent, or Firm—Jones & Askew, LLP (57) ABSTRACT

Nucleotide sequences of cotton plant cDNA clones randomly selected are determined. Homology search is performed between the sequences and known gene sequences registered in the data base. Thus a gene, which controls the fiber formation mechanism in cotton plant and which can be used for industrially useful improvement, is isolated from clones having homology to a gene in the data base.

10 Claims, 3 Drawing Sheets

```
5'    AATTCGGCACGAG  3'
3'        GCCGTGCTC  5' ---
```

1 Seedling (5 days old)
2 Root (10 days old)
3 Cotyledon (5 days old)
4 Leaf
5 Fiber (10 DPA)
6 Fiber (17 DPA)

Fig. 3

COTTON PLANT GENE

TECHNICAL FIELD

The present invention relates to a novel gene of cotton plant. In particular, the present invention relates to a gene which is transcribed in a large amount in fiber cells during cotton fiber formation. In particular, the present invention relates to a gene coding for an amino acid sequence having zinc finger motif, the zinc finger motif being one of characteristic sequences of transcription factors.

BACKGROUND ART

Cotton plant occupies an extremely important position as a plant for raw material supply in the textile industry as a matter of course, as well as in the paper-manufacturing industry and the food industry. Therefore, improvement of cotton plant is extensively performed. Efforts to improve cotton plant are made in various viewpoints, such as those for addition and improvement of various characteristics, including, for example, those concerning increase in oil content and improvement in disease resistance, cold resistance, drought resistance, salt tolerance, herbicide resistance, high-yielding ability, early harvest characteristics, and fiber characteristics.

Especially, improving procedures, which have been impossible by using the conventional method, are being carried out by regulating gene expression in a plant by using genetic engineering techniques. When expression of a foreign or endogeneous gene is regulated in the plant in accordance with such a method, it is desirable that the gene to be introduced has been previously isolated, or information has been previously obtained for a sequence of the gene for which expression is regulated, a sequence of an upstream region therefrom, a tissue in which the gene is expressed, and a timing or stage of expression.

As for cotton plant, a small number of genes and little genetic information are still known to be used for the techniques as described above. In such circumstances, although several study reports have been made for what kinds of genes are transcribed, translated, and expressed to what extent during fiber formation in cotton plant (M. E. John et al., *Proc. Natl. Acad. Sci. USA,* 89, 5769 (1992); T. A. Wilkins, *Plant Physiology,* 102, 679 (1993); and Din-Pow Ma et al., *BBA,* 1257, 81 (1995)), the knowledge is still insufficient. Especially, there has not been isolated any transcription factor-like gene which should be expressed in a large amount in fiber cells during cotton fiber formation.

SUMMARY OF THE INVENTION

An object of the present invention is to provide a gene which regulates the fiber formation mechanism in cotton plant, and which is used for industrially useful cotton plant through various improving procedures. Another object of the present invention is to provide a gene possibly coding for a transcription factor, expressed in a large amount in fiber cells of cotton plant during cotton fiber formation.

It is known that the transcription factor binds to a specific DNA sequence on genome, and thus it regulates transcription of a specified gene. Owing to this mechanism, the timing or stage and the location of expression of respective genes are controlled in an organized manner.

Provided that a transcription factor is expressed in a large amount in cotton plant fiber cells during cotton fiber formation, it is considered that expression of a gene of such a transcription factor is regulated in fiber cells during fiber formation, and consequently the organ of cotton fiber is formed by controlling the transcription of a gene which specifically interacts with the transcription factor, for its timing and location, i.e., during fiber formation in fiber cells.

Therefore, it is possible to control the expression of the gene which specifically interacts with the transcription factor, by controlling the expression itself of the gene coding for the transcription factor. Thus it is possible to modify the character of fiber, create fiber not known until the present, and create a seed having no fiber. In that way, it is considered that cotton plant useful for the fiber industry, the paper-manufacturing industry, and the food industry can be provided.

A gene, which is expressed in a large amount in cotton plant fiber cells during cotton fiber formation and has a transcription factor-like motif, may not actually have the function of a transcription factor. It is considered that expression of even such a gene affects the fiber formation mechanism. Accordingly, it can be expected that any effect is exerted during cotton fiber formation by controlling expression of the gene, and any improved effect appears on fiber.

Further, it is sufficiently conceivable that genes coding for polyamino acids having the zinc finger motif exist in the cotton plant gene, other than the gene of the present invention. Therefore, it is possible to isolate various genes coding for polyamino acids having the zinc finger motif, including the gene of the present invention, by using, as a probe, a sequence portion coding for the zinc finger motif. Thus it is expected that transcription of many genes can be controlled in cotton plant.

Further, a transcriptional regulatory region existing in an upstream region of the genome may be isolated by using, as a probe, a part or all of a sequence of a coding region of such a gene. An arbitrary gene may be ligated at an downstream position from the transcription regulatory region, and the obtained DNA may be introduced into the cotton gene. Thus it is also possible to express the gene in a large amount in fiber cells during fiber formation. Such an approach may be industrially useful.

The present inventors prepared a cDNA library from cotton plant. The present inventors randomly selected a large amount of clones therefrom to subsequently determine their nucleotide sequences so that homology search was performed between the determined nucleotide sequences and known gene sequences included in a gene data base. In general, a method is used for cloning a gene, in which a part or all of a gene sequence having been isolated from another organism is used as a probe to perform screening from a library. However, in the present invention, homology search was performed between the nucleotide sequences of the clones randomly selected from the cDNA library and the known gene sequences in the data base. Thus it was found that a cotton plant gene was present, having high homology to a sunflower gene SF3 considered to correspond to a transcription factor specifically expressed in sunflower pollen and having two zinc finger motifs (Rachel Baltz et al., *The Plant Journal,* 2(5), 713–721 (1992)). Further, it was found that the gene was expressed in a large amount in fiber cells, by means of northern analysis for the cotton plant gene. Thus the present invention has been completed.

Namely, the present invention lies in a DNA coding for a protein as defined in the following (A) or (B):

(A) a protein having an amino acid sequence shown in SEQ ID NO: 2; or (B) a protein comprising an amino acid sequence in which one or several amino acids are deleted, substituted, inserted, or added with respect to the sequence shown in SEQ ID NO: 2, and comprising a polyamino acid having a zinc finger motif.

The nucleotide sequence of the DNA of the present invention is specifically exemplified by DNA as defined in the following (a) or (b):

(a) a DNA having a sequence of nucleotide numbers of 134 to 757 in SEQ ID NO: 1; or
(b) a DNA which is hybridizable with the DNA as defined in the foregoing item (a) under a stringent condition and which codes for a protein comprising a polyamino acid having a zinc finger motif.

The DNA is a gene which is expressed in a large amount in fiber cells during cotton fiber formation. In particular, the DNA is a gene which codes for an amino acid sequence having a zinc finger motif as one of characteristic sequences of the transcription factor. The gene is herein referred to as "the gene of the present invention", if necessary.

In another aspect of the present invention, there is provided a DNA probe as a probe for hybridization, used to isolate a transcription regulatory region of a gene expressed during cotton fiber formation, and used to isolate various genes coding for polyamino acids having zinc finger motifs, including the gene of the present invention, the DNA probe comprising a part or all of the gene of the present invention.

The homology between the amino acid sequence encoded by the gene of the present invention and the amino acid sequence encoded by the sunflower gene SF3 is found at the portion of zinc finger motif and the portion of basic domain. The repeating sequences of pentapeptides located at the C-terminal, which are characteristic of the amino acid sequence encoded by the sunflower gene SF3, are not present in the amino acid sequence encoded by the cotton plant gene. In place of the repeating sequences, the gene of the present invention has a sequence which is abundant in threonine and alanine. Further, the gene of the present invention is different from the sunflower gene SF3 in the number of amino acids encoded thereby. Therefore, it is considered that the amino acid sequence encoded by the gene of the present invention is a transcription factor which has a function different from that of the amino acid sequence encoded by the sunflower gene SF3. It is expected that the gene of the present invention can be used as a probe for hybridization, used to isolate a transcription regulatory region of a gene expressed during cotton fiber formation, and as a probe for hybridization, used to isolate various genes coding for polyamino acids having zinc finger motifs, including the gene of the present invention.

DETAILED DESCRIPTION OF THE INVENTION

The present invention will be explained in detail below.

The gene of the present invention has been obtained for the first time according to a method described below, and its amino acid sequence and nucleotide sequence have been clarified by the present invention. Accordingly, the gene of the present invention can be also obtained with ease on the basis of the amino acid or nucleotide sequence in accordance with any method known to those skilled in the art, such as those based on amplification from chromosomal DNA, cDNA, or mRNA by means of the PCR method, and screening from a library by means of the hybridization method.

An illustrative method for obtaining the gene of the present invention will be explained for each of its steps.

<1> Preparation of Gene Library

The gene library can be prepared from either chromosomal DNA or mRNA. However, in order to efficiently isolate and identify the structural gene, it is desirable to prepare a cDNA library by using mRNA as a material.

The gene of the present invention is expressed in a large amount in fiber cells of cotton plant during cotton fiber formation. Therefore, it is preferable to use fiber cells of cotton plant during cotton fiber formation, as a material for extracting mRNA. Any method for extracting mRNA can be used without any special limitation. It is possible to adopt ordinary methods for extracting mRNA from plant.

cDNA can be synthesized, for example, by synthesizing complementary DNA with reverse transcriptase while using, as a primer, a poly-T sequence complementary to poly-A nucleotide existing at the terminal of mRNA, and forming a double strand with DNA polymerase.

The method for synthesizing cDNA is described, for example, in "Molecular Cloning" (Maniatis et al., Cold Spring Harbour Laboratory). However, a lot of cDNA synthesis kits are commercially available from various companies. Therefore, it is convenient to use such a kit.

The library is generally constructed by using a phage vector. It is possible to use a lot of commercially available vectors. However, it is preferable to use a vector such as λZAP vector with which it is unnecessary to perform recloning from the vector, and it is possible to immediately prepare a plasmid for sequencing.

<2> Determination of Sequence of Genes

Clones are randomly selected from the obtained gene library to determine nucleotide sequences of inserts in the clones. The nucleotide sequence can be determined in accordance with the Maxam-Gilbert method or the Dideoxy method. Especially, the Dideoxy method is more convenient and preferred.

In order to determine the nucleotide sequence in accordance with the Dideoxy method, it is possible to use a commercially available sequencing kit. Further, it is possible to determine sequences of a large number of clones in a short period of time by using an automatic sequencer.

It is unnecessary to determine the sequence for its entire length for each of the inserts. It is sufficient to determine the sequence for a length considered to be enough to perform homology search. For example, in the embodiment described later on, the homology search described below was performed when sequences of not less than 60 nucleotides were successfully determined.

<3> Homology Search with Gene Data Base

The determined nucleotide sequences of the respective cDNA clones are subjected to homology search with respect to known nucleotide sequences registered in the gene data base.

It is possible to utilize, as the data base, for example, GenBank, EMBL, and DDBJ provided by Los Alamos National Institute, United States; Institute of Molecular Biology, Europe; and National Institute of Genetics, Japan. It is possible to purchase and use, as a program for homology search, commercially available DNA analysis softwares such as DNASIS (Hitachi Software Engineering Co., Ltd.) and GENETYX (SDC Software Development). Another method is also available, in which a terminal computer is connected to a host computer in National Institute of Genetics to perform homology search at a high speed.

The homology search is performed, for example, in accordance with the following algorithm. The homology is successively compared while shifting a sequence to be investigated by every one nucleotide with respect to individual gene sequences in the data base. When six or more continuous nucleotides are coincident, the homology score is calculated in accordance with a homology score table (for example, see M. Dayhoff, "Atlas of Protein Sequence and Structure", vol. 5 (1978)). The routine is set such that those having a score of not less than a certain value are picked up as candidates having homology. It is preferable to introduce gaps into the sequence to be investigated or into the gene sequences in the data base to make optimization so that the score is maximized.

As shown in the embodiment described later on, the gene of the present invention has been obtained as one of a large number of genes having homology to a known gene. The gene of the present invention is acknowledged to have homology to the sunflower gene SF3 which is considered to be a transcription factor specifically expressed in sunflower pollen and having two zinc finger motifs. As a result of comparison for the nucleotide sequence in the coding region, the gene has homology of 72.8%. As a result of comparison for the amino acid sequence deduced from the nucleotide sequence, the gene has homology of 62.9%. The gene of the present invention also has the zinc finger motif portion and the basic domain portion with reference to the result of analysis for the sunflower gene SF3 (Rachel Baltz et al., *The Plant Journal*, 2(5), 713–721 (1992)). Accordingly, it is considered that the gene of the present invention also has a function as a transcription factor.

<4> Isolation of Full Length Clone of Cotton Plant Gene Having Homology to Gene in Gene Data Base The clone obtained as described above not necessarily includes entire nucleotide sequences of the gene. In such a case, the clone is used as a probe to perform screening by means of plaque hybridization. Thus it is possible to obtain a clone including a full length gene from the library. As for a specified method, reference may be made to "Molecular Cloning", 2nd edition, (Maniatis et al., Cold Spring Harbour Laboratory) 12.30–12.40.

In the embodiment, a clone having a full length was successfully obtained from randomly selected cDNA clones. Therefore, it was unnecessary to perform rescreening. However, the clone having the full length can be easily screened from the library by selecting an appropriate oligonucleotide sequence from a 5'-noncoding region (nucleotide numbers 1 to 133) shown in SEQ ID NO: 1, and using it as a probe. Alternatively, a DNA fragment having the entire length may be obtained by ligating a plurality of clones having partial sequences.

<5> Northern Analysis for Gene

Hybridization is performed with respect to total RNA extracted from respective tissues of cotton plant at respective stages, by using the clone obtained as described above as a probe to carry out Northern analysis in order to investigate at what stage the gene is expressed in what tissue. Specifically, Northern analysis may be performed with reference to "Molecular Cloning", 2nd edition (Maniatis et al., Cold Spring Harbour Laboratory) 7.37–7.52.

The knowledge has been obtained by the Northern analysis that the gene of the present invention is expressed in a large amount in fiber cells of cotton plant 17 days post anthesis.

A nucleotide sequence of the gene of the present invention obtained as described above, and an amino acid sequence deduced from the nucleotide sequence are shown in SEQ ID NOs. 1 and 2 in Sequence Listing. The amino acid sequence is a novel sequence. All genes having nucleotide sequences coding for the amino acid sequence are included in the present invention. The amino acid sequence may undergo deletion, substitution, insertion, and/or addition of one or several amino acid residues provided that the characteristic of the gene of the present invention is not substantially affected. The number of the several amino acid residues may be a number to give homology of not less than 80% with respect to the amino acid sequence shown in SEQ ID NO: 2. Those including such deletion, substitution, insertion, and/or addition of one or several amino acid residues can be obtained as those having the activity of the transcription factor in fiber cells of cotton plant during cotton fiber formation, or as those expressed in a large amount in fiber cells of cotton plant during cotton fiber formation, selected from expression products of DNAs of genes modified randomly by means of an ordinary mutation treatment or intentionally by means of the site-directed mutagenesis method. Those harboring proteins or genes having sequences partially different from the sequence shown in the Sequence Listings may exist depending on the variety of cotton plant or depending on natural mutation or the like. Such genes (variants) are also included in the gene of the present invention. These genes can be obtained as nucleotide sequences coding for the amino acid sequence shown in SEQ ID NO: 2 or a part thereof, nucleotide sequences coding for amino acid sequences subjected to mutation as described above. More specifically, these genes can be obtained as DNA hybridizable, under a stringent condition, with DNA having a sequence of nucleotide numbers of 134 to 757 in SEQ ID NO: 1 or a part thereof. By the "stringent condition" referred to herein is meant a condition under which a specific hybrid is formed, and nonspecific hybrid is not formed. It is difficult to clearly express the condition with numerical values. However, the condition is exemplified by a condition under which, nucleic acid having high homology, for example, DNA's having homology of not less than 80% are hybridized with each other, and nucleic acids having homology lower than the above are not hybridized with each other. The DNA hybridizable under the stringent condition will code for the protein comprising the polyamino acid having the zinc finger motif at a high probavility.

<6> Utilization of the Gene of the Present Invention

The gene of the present invention makes it possible to control the mechanism for forming fiber in cotton plant, and control the gene expression mechanism effected by the polyamino acid having the zinc finger motif. Thus it is expected to utilize the gene of the present invention for creating industrially useful cotton plant.

Specifically, a DNA sequence coding for a specified polypeptide is ligated to the transcription regulatory region located in the upstream region of the gene of the present invention, and an obtained fragment is introduced into cotton plant. Thus it is possible to express the polypeptide in a large amount during fiber formation. It is also expected to create a seed having no fiber by introducing an antisense gene of the gene of the present invention into cotton plant.

Various genes coding for polyamino acids having zinc finger motifs including the gene of the present invention, isolated by using the gene sequence of the present invention, or antisense genes of such various genes may be introduced into cotton plant after being ligated at a position downstream from the transcription regulatory region containing a promoter originating from any one of various plant genes. Thus it is possible to control expression of such genes. The amount of expression of a gene product itself of such a gene may be changed, and consequently expression of a gene controlled by such a gene product may be changed. Thus it is expected that cotton plant improvement can be performed.

The gene of the present invention is expressed in a large amount during cotton fiber formation, and the polyamino acid having the zinc finger motif is considered to be a transcription factor. Therefore, the gene of the present invention can be used as a probe for hybridization for isolating its transcription regulatory region, and a probe for hybridization for isolating a gene coding for a polyamino acid having the zinc finger motif. As for the method for this purpose, it is preferable to use a screening method similar to the method used to isolate the entire length clone of the gene of the present invention. In such a procedure, all region of the gene of the present invention may be used as the probe, or only a part thereof may be used as the probe. However, when the transcription regulatory region is isolated, it is preferable to use a portion other than those coding for the zinc finger motif (The zinc finger motifs are located in nucleotide number 164 to 253 and 458 to 547 in SEQ ID NO: 1). When various genes coding for polyamino acids having the zinc finger motif, including the gene of the present invention, are isolated, it is preferable to use the sequence coding for the zinc finger motif as the probe (for example, a sequence corresponding to nucleotide number 164 to 253 and 458 to 547 in SEQ ID NO: 1).

According to the present invention, the gene which is transcribed in a large amount in fiber cells during fiber formation of cotton plant, especially, the gene which codes for the amino acid sequence having a zinc finger motif as one of characteristic sequences of the transcription factor has been obtained for the first time. It is expected that the gene regulates the fiber formation mechanism in cotton plant, and the gene is used for industrially useful cotton plant improvement.

BRIEF DESCRIPTION OF THE DRAWINGS

In FIG. 3, lane 1: seedling on 5th day after germination (seedling (5 days old)); lane 2: root on 10th day after germination (root (10 days old)); lane 3: cotyledon on 5th day after germination (cotyledon (5 days old)); lane 4: mature leaf (leaf); lane 5: fiber cells on 10th day post anthesis (fiber (10 DPA); and lane 6: fiber cells on 17th day post anthesis (fiber (17 DPA)).

DESCRIPTION OF THE PREFERRED EMBODIMENTS

Embodiments of the present invention will be explained below.

<1> Preparation of Total RNA From Cotton Plant

Cotton plant (*Gossypium hirsutum* L.) Coker 312 was used as a material, and its fiber cells were collected in liquid nitrogen. The fiber cells (75 g) of cotton plant were sufficiently ground in a mortar while being frozen in liquid nitrogen. The fiber obtained in a form of powder was transferred to a centrifuge tube equipped with a cap, and 375 mg of DTT in a form of powder was added thereto. After that, 200 ml of XT buffer (0.2 M sodium borate containing 30 mM EDTA and 1% SDS was adjusted to have pH 9.0, followed by a treatment with diethylpyrocarbonate and autoclave to obtain a solution and vanadyl ribonucleoside was added to the solution to give a concentration of 10 mM) heated to 90 to 95° C. was added and sufficiently agitated.

To the solution, 100 mg of protease K was added, and it was agitated again. The solution was incubated at 40° C. for 2 hours, and then 16 ml of 2 M KCl was added thereto. The solution was sufficiently agitated again, and then it was left to stand in ice for 1 hour. The solution was centrifuged for 20 minutes at 4° C. at 12,000 g by using a high speed cooling centrifuge.

An obtained supernatant was filtered to remove floating materials, and the solution was transferred to a messcylinder to measure its volume. The solution was transferred to another centrifuge tube, and lithium chloride was added in a ratio of 85 mg per ml the extract solution to give a final concentration of 2 M. The solution was left to stand at 4° C. overnight. After that, precipitated RNA was centrifuged for 20 minutes at 12,000 g. The obtained precipitate of RNA was washed and precipitated twice with cold 2 M lithium chloride.

Obtained RNA was dissolved in 10 mM Tris buffer (pH 7.5) to be about 2 mg/ml, and 5 M potassium acetate was added thereto to give a concentration of 200 mM, and then ethanol was added to give a concentration of 70%, followed by being cooled at −80° C. for 10 minutes. The solution was centrifuged at 4° C. at 15,000 rpm for 10 minutes, and then a precipitate was suspended in an appropriate amount of sterilized water to obtain an RNA sample. As a result of quantitative determination for the RNA sample, 2 mg of total RNA was obtained.

<2> Purification of mRNA mRNA was purified as a poly(A)$^+$ RNA fraction from the total RNA obtained as described above. Purification was performed by using Oligotex-dT30 <Super> (purchased from Toyobo) as oligo (dT)-immobilized latex for purifying poly(A)$^+$ RNA.

Elution buffer (buffer for elution: 10 mM Tris-HCl (pH 7.5), 1 mM EDTA, 0.1% SDS) was added to a solution containing 1 mg of total RNA to give a total volume of 1 ml, and 1 ml of Oligotex-dT30 <Super> was added thereto. Heating was performed at 65° C. for 5 minutes, followed by quick cooling on ice for 3 minutes. To the solution, 0.2 ml of 5 M NaCl was added, and it was incubated at 37° C. for 10 minutes. After that, the solution was centrifuged at 15,000 rpm for 3 minutes, and then a supernatant was carefully removed.

An obtained pellet was suspended in 2.5 ml of Washing Buffer (10 mM Tris-HCl (pH 7.5), 1 mM EDTA, 0.5 M NaCl, 0.1% SDS). The solution was centrifuged at 15,000 rpm for 3 minutes, and then a supernatant was carefully removed. An obtained pellet was suspended in 1 ml of TE Buffer (10 mM Tris-HCl (pH 7.5), 1 mM EDTA), followed by being heated at 65° C. for 5 minutes. The solution was quickly cooled on ice for 3 minutes, and then it was centrifuged at 15,000 rpm for 3 minutes to recover poly(A)$^+$ mRNA in the supernatant.

About 10 μg of poly(A)$^+$ mRNA was obtained from 1 mg of total RNA as described above. 5 μg of the obtained poly(A)$^+$ mRNA was used to prepare a cDNA library.

<3> Preparation of cDNA Library (1) Synthesis of cDNA cDNA was synthesized by using mRNA obtained as described above as a template, and using λZAP cDNA synthesis kit produced by Stratagene.

The following solutions were mixed in a tube.

5.0 µl 10× 1st Strand Buffer (buffer for reverse transcription reaction);

3.0 µl 10 mM 1st Strand Methyl Nucleotide Mix (mixture of A, G, C, and U);

2.0 µl Linker-Primer (primer also used as linker);

$H_2O$ (to adjust to have a whole volume of 50 µl);

1.0 µl RNase Block II (RNase inhibitor).

The respective components described above were contents of the kit. Linker-Primer had a sequence as shown in SEQ ID NO: 3. Methylated nucleotide was used so that cDNA might not be digested during the restriction enzyme reaction performed later on.

The reaction solution was sufficiently agitated, and then 5.0 µg of the poly(A)$^+$ mRNA was added thereto, followed by being left to stand at room temperature for 10 minutes. Further, 2.5 µl of M-MuLV RTase (reverse transcriptase) was added (at this time, the whole volume was 50 µl). The solution was mixed slowly. After that, gentle centrifugation was performed to allow the reaction solution to drop down to the bottom of the tube so that the reaction was made at 37° C. for 60 minutes.

Next, the following solutions were mixed in the tube in accordance with the prescribed order.

45.0 µl reaction solution containing cDNA first strand;

40.0 µl 10× 2nd Strand Buffer (buffer for polymerase reaction);

6.0 µl 2nd Strand Nucleotide Mixture (mixture of A, G, C, and T);

302.0 µl $H_2O$.

The following solutions were further added. However, in order to allow RNase and DNA polymerase to simultaneously begin to work, the enzyme solutions were affixed to the wall of the tube. After that, the tube was promptly subjected to a vortex treatment followed by centrifugation so that the reaction solution was allowed to drop down to the bottom of the tube to perform a reaction for synthesizing cDNA second strand at 16° C. for 150 minutes.

0.8 µl RNase H (RNA-degrading enzyme);

7.5 µl DNA polymerase I (10.0 u/µl).

To the solution, 400 µl of a mixture of phenol:chloroform (1:1) was added. The solution was sufficiently agitated, and then it was centrifuged at room temperature for 2 minutes. To an obtained supernatant, 400 µl of phenol:chloroform was added, and it was subjected to a vortex treatment. The solution was centrifuged at room temperature for 2 minutes. To an obtained supernatant, the following solutions were added to precipitate cDNA:

33.3 µl 3 M sodium acetate solution;

867.0 µl 100% ethanol.

The solution was left to stand at −20° C. overnight. The solution was centrifuged at room temperature for 60 minutes, followed by gentle washing with 80% ethanol and centrifugation for 2 minutes. A supernatant was removed, and a resultant pellet was dried. The pellet was dissolved in 43.5 µl of sterilized water. To 39.0 µl of an obtained solution, the following solutions were added to blunt-end cDNA terminals.

5.0 µl 10× T4 DNA Polymerase Buffer (buffer for T4 polymerase reaction);

2.5 µl 2.5 mM dNTP Mix (mixture of A, G, C, and T);

3.5 µl T4 DNA polymerase (2.9 u/µl).

The reaction was performed at 37° C. for 30 minutes. To the solution, 50 µl of sterilized water was added, and then 100 µl of phenol:chloroform was added. The solution was subjected to a vortex treatment, and it was centrifuged for 2 minutes. To an obtained supernatant, 100 µl of chloroform was added, and it was subjected to a vortex treatment, followed by centrifugation for 2 minutes. To an obtained supernatant, the following solutions were added to precipitate cDNA.

7.0 µl 3 M sodium acetate solution;

226 µl 100% ethanol.

Figure 1:
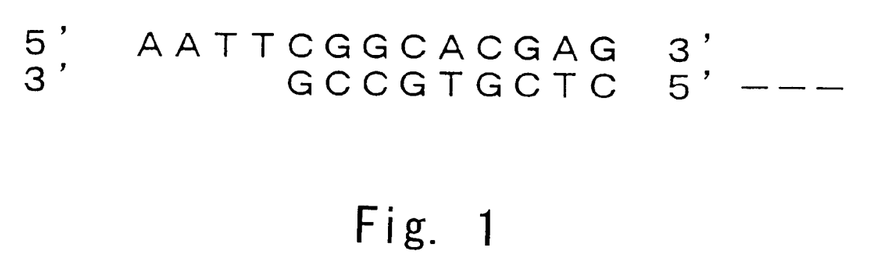
FIG. 1 shows a structure of EcoRI adapter.

The solution was left to stand on ice for not less than 30 minutes, and it was centrifuged at 4° C. for 60 minutes. An obtained precipitate was washed with 150 µl of 80% ethanol. The solution was centrifuged for 2 minutes, and then the precipitation was dried. An obtained cDNA pellet was dissolved in 7.0 µl of a solution of EcoRI Adaptor (EcoRI adapter, see FIG. 1). Further, the following solutions were added to ligate EcoRI adapters to both ends of cDNA.

1.0 µl 10× Ligation Buffer (buffer for ligase reaction);

1.0 µl 10 mM ATP;

1.0 µl T4 DNA ligase.

The reaction solution was gently centrifuged, and it was left to stand at 4° C. for overnight or more. Sequences of respective strands of EcoRI adapter are shown in SEQ ID NOs: 4 and 5 and FIG. 1. The solution was treated at 70° C. for 30 minutes, and then it was gently centrifuged, followed by being left to stand at room temperature for 5 minutes. To the solution, the following solutions were added to phosphorylate the 5'-terminal of EcoRI adapter.

1.0 µl 10× Ligation Buffer (buffer for ligase reaction);

2.0 µl 10 mM ATP;

6.0 µl $H_2O$;

1.0 µl T4 polynucleotide kinase (10.0 u/µl).

The reaction was performed at 37° C. for 30 minutes, and then the solution was treated at 70° C. for 30 minutes. After that, the solution was gently centrifuged, and it was left to stand at room temperature for 5 minutes.

To the solution, the following solutions were further added to perform a reaction at 37° C. for 90 minutes. Thus the XhoI site introduced by Linker-Primer was digested with XhoI, followed by being left to stand at room temperature to cool the solution.

28.0 µl XhoI buffer;

3.0 µl XhoI (45 u/µl).

To the reaction solution, 5.0 µl of 10× STE (10 mM Tris-HCl (pH 8.0), 100 mM NaCl, 1 mM EDTA) was added, and it was placed in a centrifuge column (Sephacryl Spin Column) for removing short fragments, followed by centrifugation at 600 g for 2 minutes to obtain an eluted solution which was designated as Fraction 1. This operation was further repeated three times to obtain eluted solutions which were designated as Fractions 2, 3, and 4 respectively.

Fractions 3 and 4 were combined into a solution, and phenol:chloroform (1:1) was added thereto. The mixture was sufficiently agitated, followed by centrifugation at room temperature for 2 minutes. To an obtained supernatant, an equal amount of chloroform was added, and the solution was sufficiently agitated. The solution was centrifuged at room temperature for 2 minutes to obtain a supernatant and a 2-fold amount of 100% ethanol was added to the supernatant, followed by being left to stand at −20° C. overnight. The solution was centrifuged at 4° C. for 60 minutes, followed by washing with an equal amount of 80% ethanol. Centrifugation was further performed at 4° C. for 60 minutes to obtain a pellet of cDNA and the pellet was suspended in 10 µl of sterilized water.

(2) Preparation of cDNA Library

Double strand cDNAs obtained as described above were ligated with a λ phage expression vector to prepare recombinant vectors.

The following solutions were mixed in a tube to make a reaction at 12° C. overnight, followed by being left to stand at room temperature for 2 hours to ligate cDNA with the vector.

| | |
|---|---|
| 2.5 µl | cDNA solution; |
| 0.5 µl | 10X Ligation Buffer; |
| 0.5 µl | 10 mM ATP; |
| 1.0 µl | λZAP vector DNA (1 µg/µl); |
| 0.5 µl | T4 DNA ligase (4 Weiss µ/µl). |

(3) Packaging of Phage DNA Into Phase Particles

Phage vectors inserted with cDNA's were packaged into phage particles by using an in vitro packaging kit (Gigapack II Gold packaging extract: produced by Stratagene).

To freeze/Thaw extract immediately after dissolution, the recombinant phage solution was added, and it was placed on ice. To the solution, 15 µl of an extract for ultrasonic treatment (Sonic extract) was immediately added, and it was sufficiently mixed by means of pipetting. The solution was gently centrifuged, followed by being left to stand at room temperature (22° C.) for 2 hours.

To the reaction solution, 500 µl of Phage Dilution Buffer and 20 µl of chloroform were added, followed by mixing. In order to measure the titer of the library, 2 µl of 500 µl of aqueous phase was diluted 1:10 with 18 µl of SM buffer (NaCl 5.8 g, $MgSO_4 \cdot 7H_2O$ 2 g, 1 M Tris-HCl (pH 7.5) 50 ml, 2% gelatin 5 ml in 1 L). 1 µl of the diluted solution and 1 µl of the nondiluted phage solution were plated respectively together with 200 µl of a liquid culture of *Escherichia coli* PLK-F' strain having been cultivated until $OD_{600}$ was 0.5. Namely, *Escherichia coli* PLK-F' strain was mixed with the phage solution, which was cultivated at 37° C. for 15 minutes. The culture was added to 2 to 3 ml of top agar (48° C.), and it was immediately overlaid on NZY agar plate warmed at 37° C. Cultivation was performed at 37° C. overnight, and the number of appeared plaques was counted to calculate the titer. As a result, the titer was $1.2 \times 10^6$ pfu/ml.

(4) Amplification of Library

To a centrifuge tube, the packaging solution containing about 50,000 recombinant bacteriophages and 600 µl of a liquid culture of *Escherichia coli* PLK-F' strain having been cultivated until $OD_{600}$ was 0.5 were added, followed by cultivation at 37° C. for 15 minutes. To an obtained liquid culture, 6.5 ml of top agar previously kept at 48° C. after dissolution was added, and it was overlaid on NZY plate (150 mm) previously warmed at about 37° C. Cultivation was performed at 37° C. for 5 to 8 hours. To each of the plates, 10 ml of SM buffer was added, followed by cultivation at 4° C. overnight with slow shaking.

SM Buffer solutions in the respective plates were collected in a sterilized polypropylene tube. The respective plates were rinsed with 2 ml SM buffer, and rinsed solutions were also collected in the same tube. Chloroform in an amount corresponding to 5% of the total amount was added and mixed, followed by being left to stand at room temperature for 15 minutes. Centrifugation was performed at 4,000 g for 5 minutes to remove bacterial cells. To an obtained supernatant, chloroform was added in an amount corresponding to 0.3% of the total amount, and it was stored at 4° C.

The titer of a library thus amplified was measured in the same manner as described above. As a result, the titer was $2.3 \times 10^9$ pfu/ml.

(5) Excision of Plasmid From Phase DNA

In vivo excision of the plasmid portion from recombinant phage DNA was performed (In vivo Excision). The following materials were mixed in a 50 ml conical tube to effect infection at 37° C. for 15 minutes.

*Escherichia coli* XL1-Blue liquid culture ($OD_{600}=0.1$) 200 µl;

phage solution after amplification 200 µl ($>1 \times 10^5$ phage particles);

helper phage R408 1 µl ($>1 \times 10^6$ pfu/ml).

To the mixed solution, 5 ml of 2× YT medium was added, followed by cultivation with shaking at 37° C. for 3 hours. The culture was heat-treated at 70° C. for 20 minutes, followed by centrifugation at 4,000 g for 5 minutes. A supernatant was decanted and transferred to a sterilized tube. The solution in the tube was centrifuged to obtain a supernatant. 20 µl of a solution obtained by diluting the supernatant 100 times was mixed with 200 µl of a liquid culture of *Escherichia coli* XL1-Blue having been cultivated until $OD_{600}$ was 1.0, and infection was effected at 37° C. for 15 minutes.

1 to 100 µl of the liquid culture was plated on LB plates containing ampicillin, followed by cultivation at 37° C. overnight. Appeared colonies were randomly selected. Glycerol was added thereto and they were stored at −80° C.

(6) Preparation of Plasmids

Respective plasmids were prepared by using Magic miniprep kit produced by Promega.

Each of liquid cultures of *Escherichia coli* strains harboring the plasmids stored at −80° C. was inoculated to 5 ml of 2× YT medium, followed by cultivation at 37° C. overnight. Centrifugation was performed for 5 minutes (4,000 rpm, 4° C.) to decant and remove a supernatant. To an obtained bacterial cell pellet, 1 ml of TE buffer was added, and it was subjected to a vortex treatment. An obtained bacterial cell suspension was transferred to an Eppendorf tube, followed by centrifugation for 5 minutes (5,000 rpm, 4° C.). A resultant supernatant was decanted and removed.

To the bacterial cell pellet, 300 µl of Cell Resuspension Solution (solution for suspending cells) was added. The pellet was sufficiently suspended therein, and an obtained suspension was transferred to an Eppendorf tube. The suspension was agitated with a mixer for 2 minutes. 300 µl of Cell Lysis Solution (solution for lysing cells) was added thereto and agitation was performed until the suspension became transparent. Further, 300 µl of Neutralization Solution (solution for neutralization) was added thereto, and it was agitated by shaking with hand, followed by centrifugation (15,000 rpm) for 10 minutes.

Only an obtained supernatant was transferred to a new Eppendorf tube (1.5 ml). A cock, a miniature column, and a syringe were connected to a suction tube in this order, and a resin (1 ml) was added to the syringe.

The supernatant was injected into the syringe, and it was sufficiently agitated followed by suction. 2 ml of Column Wash Solution (solution for washing the column) was added thereto to perform washing by suction. Suction was continued in this state in order to perform drying up. The miniature column was detached, and it was set in a new Eppendorf tube (1.5 ml). 100 µl of sterilized water previously warmed to 65 to 70° C. was injected into the miniature column, and the column was subjected to centrifugation (5,000 rpm) for 1 minute together with the Eppendorf tube.

An eluted solution was transferred to the Eppendorf tube. 5 µl of 3 M sodium acetate aqueous solution was added thereto, and 250 μl of cold ethanol was added. An obtained solution was centrifuged (15,000 rpm, 25 minutes), and a supernatant was discarded. To an obtained precipitate, 1 ml of 70% ethanol was added, and it was centrifuged again (15,000 rpm, 3 minutes). Ethanol was completely eliminated, and the tube was vacuum-dried in a desiccator. The precipitate was sufficiently dissolved in 20 μl of sterilized water, and it was stored at −20° C. 1 μl of this solution was used to perform electrophoresis together with volume markers so that the plasmid DNA was quantitatively determined.

<4> Determination of Nucleotide Sequence of cDNA and Homology Search With Gene Data Base (1) Determination of Nucleotide Sequence of cDNA Nucleotide sequences of cDNAs were analyzed by using an automatic sequencer 373A produced by Applied Biosystems Inc. (ABI). The sequencing reaction was performed by using T3 primer based on the use of Dye Primer Cycle Sequencing kit produced by the same company in accordance with the appended manual. About 750 clones were randomly selected, and nucleotide sequences of them were determined.

(2) Homology Search with Gene Data Base

The determined nucleotide sequences were analyzed by using a function of homology search of a DNA analysis software, DNASIS (Hitachi Software Engineering Co., Ltd.). GenBank was selected as the data base. The algorithm for homology search was as follows. Namely, comparison was made while shifting a sequence to be investigated by every one nucleotide with respect to the sequences included in the data base. When six or more continuous nucleotides were coincident, the homology score was calculated in accordance with a homology score table. The routine was set such that those having a homology score of not less than 160 points were picked up as candidates. Further, gaps were introduced so that the score was maximized.

Of the sequences of about 750 clones subjected to the search, 321 clones had any homology to any sequence in the data base. Among them, a clone was found, which had homology to the sunflower gene SF3 considered to be the transcription factor specifically expressed in sunflower pollen and having two zinc finger motifs. The obtained clone and the sunflower gene SF3 were compared with each other. Thus it was revealed at this time point that the clone contained an initiation codon.

(3) Determination of Entire Length Nucleotide Sequence

In order to determine an entire length sequence for the clone revealed to have homology to the sunflower gene SF3 and contain the initiation codon, nucleotide sequence determination was performed by using an automatic sequencer (model 4000L) produced by LI-COR, Inc. T3 primer was used for sequencing from the 5'-terminal, and T7 primer was used for sequencing from the 3'-terminal. Thus the entire nucleotide sequence was clarified as shown in SEQ ID NO: 1.

(4) Comparison Between the Gene of the Present Invention and Sunflower Gene SF3

Homology to the sunflower SF3 gene was analyzed by using the entire sequence of the gene of the present invention having been clarified.

As a result, the nucleotide length of the coding region was 627 bp including a stop codon in the case of the gene of the present invention, while the length of the coding region was 660 bp including a stop codon in the case of the sunflower SF3 gene, giving 72.8% of homology therebetween. When comparison was made with amino acids deduced from the nucleotide sequences of the genes, the gene of the present invention had 208 amino acids, while the sunflower SF3 gene had 219 amino acids, giving 62.9% of homology therebetween.

Figure 2:
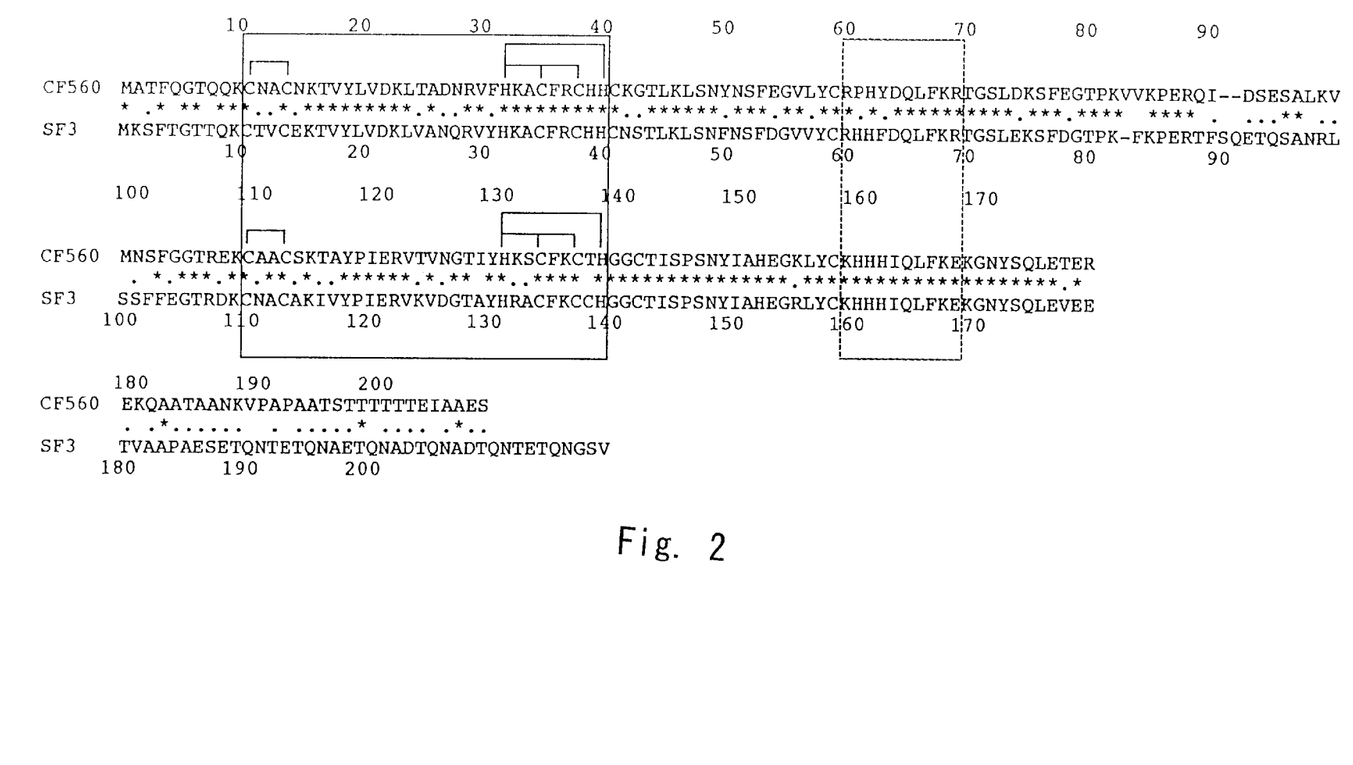
FIG. 2 shows comparison of amino acid sequences between the cotton gene of the present invention and the sunflower gene SF3, wherein a symbol "*" indicates an amino acid residue coincident between the both amino acid sequences, and a symbol "." indicates an amino acid residue having a similar property, and wherein a portion surrounded by solid lines indicates the zinc finger domains, and a portion surrounded by dotted lines indicates the basic domains.

FIG. 2 shows comparison between the respective amino acid sequences deduced from the nucleotide sequences of the gene of the present invention and the sunflower SF3 gene respectively. In FIG. 2, a symbol "*" indicates an amino acid residue coincident between the both amino acid sequences, and a symbol "." indicates an amino acid residue having a similar property. A portion surrounded by solid lines indicates the zinc finger domains, and a portion surrounded by dotted lines indicates the basic domains. An amino acid sequence deduced from the nucleotide sequence of the sunflower SF3 gene is shown in SEQ ID NO: 6.

The portion identified as the zinc finger domain surrounded by solid lines may be compared as follows. Namely, each of the genes has two domains, in which two cysteine residues (C) are included at the N-terminal side of the domain, and two histidine residues (H) and two cysteine residues (C) are included at the C-terminal side of the domain. Accordingly, as described by Rachel Baltz et al. (*The Plant Journal*, 2(5), 713–721 (1992)), it is considered that the gene possibly has the zinc finger structure of three types, i.e., $C_2$—$C_2$ type ($CX_2CX_{20}CX_2C$, X indicates an arbitrary amino acid), $C_2$—$H_2$ type ($CX_2CX_{17}HX_7H$, X indicates an arbitrary amino acid), and $C_2$—HC type ($CX_2CX_{17}HX_2C$, X indicates an arbitrary amino acid).

The basic domain is frequently found in the transcription factor having the zinc finger structure (Y.-H. Fu et al., *Mol. Cell. Biol.*, 10, 1056–1065 (1990)). Also in this case, the basic domains exist at two places corresponding to the portion surrounded by the dotted lines, in both of the gene of the present invention and the sunflower SF3 gene.

However, the gene of the present invention does not have the six times repeating sequence of pentapeptide (S,T,A) (E,D) TQN which is possessed by the sunflower SF3 gene at the C-terminal side. Instead, the gene of the present invention has a sequence abundant in threonine (T) and alanine (A). Accordingly, it is considered that the gene of the present invention has a different function from that of the sunflower SF3 gene.

<5> Northern Analysis For the Gene

Total RNAs were extracted from respective tissues of cotton plant (seedling on 5th day after germination, cotyledon on 5th day after germination, root on 10th day after germination, mature leaf, fiber cells on 10th day post anthesis, fiber cells on 17th day post anthesis). They were applied to a gel in an amount of 25 μg for each to perform electrophoresis, followed by transfer to a nylon membrane.

The cDNA clone plasmid containing the gene of the present invention was digested with two types of restriction enzymes, XhoI and EcoRI, and the portion corresponding to the insert fragment was recovered. After that, the fragment was RI-labeled by using Random Primer DNA Labeling Kit Ver. 2 (produced by Takara Shuzo Co., Ltd.).

Figure 3:
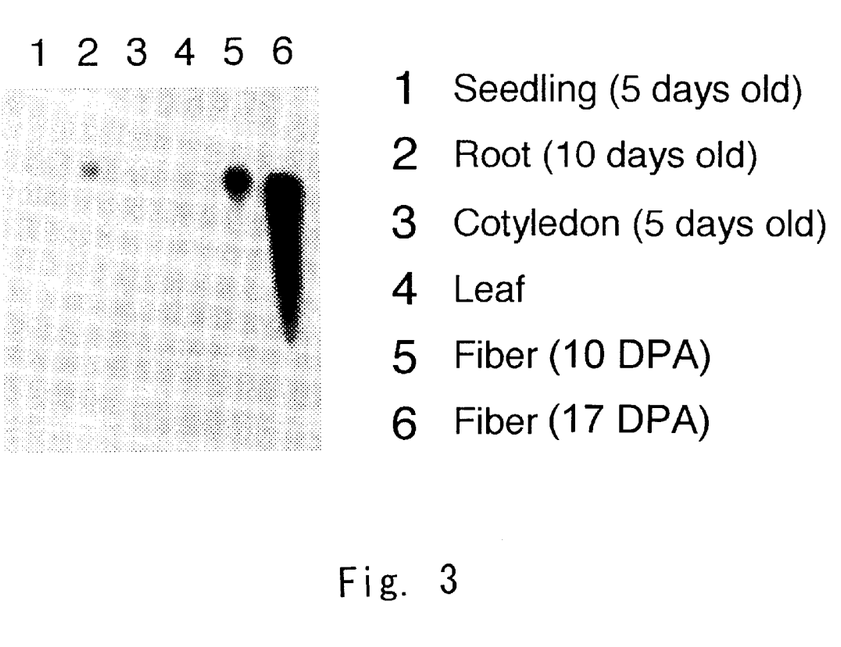
FIG. 3 shows a result of Northern hybridization for the cotton gene of the present invention (photograph after hybridization).

Northern hybridization was performed in accordance with an ordinary method by using the membrane and using the labeled insert fragment as a probe. A result is shown in FIG. 3.

According to this result, it is understood that the gene of the present invention was expressed especially in fiber cells, and in particular, it was expressed in a large amount in fiber cells on 17th day after flowering. Expression of the gene of the present invention was also observed in root on 10th day after germination. However, the amount of the expression in root was minute as compared with the expression in fiber cells. No expression of the gene of the present invention could be detected in the tissues other than the above.

What is claimed is:

1. A DNA coding for a protein comprising the amino acid sequence shown in SEQ ID No:2 or an amino acid sequence at least 80% identical to the amino acid sequence shown in SEQ ID No:2, wherein said encoded amino acid sequence is the sequence of a protein naturally occurring in *Gossypium hirsutum*.

2. The DNA according to claim 1, comprising the nucleic acid sequence shown in SEQ ID No:1 from residue 134 to residue 757 or a nucleic acid sequence at least 80% identical to the nucleic acid sequence shown in SEQ ID No:1 from residue 134 to residue 757, wherein said nucleic acid sequence encodes a protein naturally occurring in *Gossypium hirsutum*.

3. A DNA as a probe for hybridization, used to isolate transcription regulatory region regulating an expression of a gene expressed during cotton fiber formation, the DNA probe comprising all of the sequence of the DNA as defined in claim 2.

4. A method for isolating a transcription regulatory region which regulates an expression of a gene, the gene being expressed during cotton fiber formation, comprising the step of isolating the gene from a DNA library by hybridization using the DNA probe as defined in claim 3.

5. A DNA probe for hybridization, used to isolate a gene, wherein the gene encodes polyamino acids having zinc finger motifs and is expressed in cotton plant, the DNA probe comprising all of the sequence of the DNA as defined in claim 2.

6. A method for isolating a gene which encodes polyamino acids having zinc finger motifs and is expressed in cotton plant, comprising the step of isolating the gene from a DNA library by hybridization using the DNA probe as defined in claim 5.

7. A DNA probe for hybridization, used to isolate a transcription regulatory region regulating an expression of a gene expressed during cotton fiber formation, the DNA probe comprising all of the sequence of the DNA as defined in claim 1.

8. A method for isolating a transcription regulatory region which regulates an expression of a gene, the gene being expressed during cotton fiber formation, comprising the step of isolating the gene from a DNA library by hybridization using the DNA probe as defined in claim 7.

9. A DNA probe for hybridization, used to isolate a gene, wherein the gene encodes polyamino acids having zinc finger motifs and is expressed in cotton plant, the DNA probe comprising all of the sequence of the DNA as defined in claim 1.

10. A method for isolating a gene which encodes polyamino acids having zinc finger motifs and is expressed in cotton plant, comprising the step of isolation the gene from a DNA library by hybridization using the DNA probe as defined in claim 9.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1015
      (B) TYPE: nucleic acid
      (C) STRANDEDNESS: double
      (D) TOPOLOGY: linear    (ii) MOLECULE TYPE: cDNA to mRNA    (vi) ORIGINAL SOURCE:
      (A) ORGANISM: Gossypium hirsutum L.

(ix) FEATURE:
      (A) NAME/KEY: CDS
      (B) LOCATION: 134..757

(xi) SEQUENCE DESCRIPTION: SEQ ID NO:1:

```
TTTGGGTTTT GAGAAAATCA ATTCAAAACG ACTGGTTTCA CTCTTTTTTT CCTGCCTTGC        60

TGATCTTTTT GGGGTTCTTC CACAAAAAGA AACAAAAAAT TTTGGGTGAT CTGTGTTGAA       120

AAAGAAATAA AAT ATG GCG ACA TTC CAA GGA ACT CAA CAA AAA TGC AAT         169
               Met Ala Thr Phe Gln Gly Thr Gln Gln Lys Cys Asn
                 1               5                  10

GCA TGC AAC AAG ACT GTT TAT CTG GTG GAT AAG TTG ACG GCT GAT AAT         217
Ala Cys Asn Lys Thr Val Tyr Leu Val Asp Lys Leu Thr Ala Asp Asn
         15                  20                  25

AGG GTT TTT CAT AAG GCT TGC TTC CGT TGC CAC CAT TGC AAG GGT ACC         265
Arg Val Phe His Lys Ala Cys Phe Arg Cys His His Cys Lys Gly Thr
     30                  35                  40

CTC AAG CTT AGC AAC TAC AAC TCA TTT GAA GGG GTG CTA TAC TGC AGG         313
Leu Lys Leu Ser Asn Tyr Asn Ser Phe Glu Gly Val Leu Tyr Cys Arg
 45                  50                  55                  60

CCA CAC TAT GAT CAA CTC TTC AAG AGA ACT GGC AGT CTT GAC AAG AGT         361
Pro His Tyr Asp Gln Leu Phe Lys Arg Thr Gly Ser Leu Asp Lys Ser
                 65                  70                  75

TTT GAA GGA ACA CCA AAG GTT GTC AAA CCT GAA AGA CAA ATC GAT AGT         409
Phe Glu Gly Thr Pro Lys Val Val Lys Pro Glu Arg Gln Ile Asp Ser
             80                  85                  90

GAG AGT GCA CTG AAA GTG ATG AAC TCG TTT GGT GGC ACC AGA GAA AAA         457
Glu Ser Ala Leu Lys Val Met Asn Ser Phe Gly Gly Thr Arg Glu Lys
         95                 100                 105

TGT GCG GCC TGT TCT AAG ACT GCT TAT CCA ATT GAG AGG GTT ACT GTG         505
Cys Ala Ala Cys Ser Lys Thr Ala Tyr Pro Ile Glu Arg Val Thr Val
    110                 115                 120

AAT GGG ACA ATA TAC CAC AAG AGC TGC TTC AAG TGT ACC CAT GGA GGG         553
Asn Gly Thr Ile Tyr His Lys Ser Cys Phe Lys Cys Thr His Gly Gly
125                 130                 135                 140

TGT ACC ATT AGC CCA TCA AAC TAT ATA GCA CAT GAA GGT AAA CTC TAC         601
Cys Thr Ile Ser Pro Ser Asn Tyr Ile Ala His Glu Gly Lys Leu Tyr
                145                 150                 155

TGC AAA CAT CAC CAT ATC CAA CTC TTC AAG GAG AAA GGA AAC TAC AGC         649
Cys Lys His His His Ile Gln Leu Phe Lys Glu Lys Gly Asn Tyr Ser
            160                 165                 170

CAA CTC GAG ACC GAA CGA GAG AAA CAA GCC GCC ACC GCC GCC AAT AAG         697
Gln Leu Glu Thr Glu Arg Glu Lys Gln Ala Ala Thr Ala Ala Asn Lys
        175                 180                 185
```

```
GTT CCT GCC CCT GCT GCA ACA TCA ACC ACA ACC ACA ACC ACG GAG ATT      745
Val Pro Ala Pro Ala Ala Thr Ser Thr Thr Thr Thr Thr Thr Glu Ile
         190                 195                 200

GCA GCT GAG TCG TAATGATCTC AGTGTGCATC ACTGCTGCTT CAATGAAAAA          797
Ala Ala Glu Ser
205

AACTTTGTAA AACGATCCAA TGTCATTGCT GTGTTGATTT TCTGCAATGG GGTTCTTTTT    857

ATTTTTTTTC TTTGATCCAG ATATTATTCT TGGTTCATAA TATGTTACAT AAATTTCCCA    917

CTTTCAAAGA TGGGATTGAG GTGATATGTT CCAAGTGGAT TCAGCTTTTG AAAAATAAAG    977

ATTCTTTCAT TAATTCTACT AAAAAAAAAA AAAAAAA                            1015
```

(2) INFORMATION FOR SEQ ID NO:2:

(i) SEQUENCE CHARACTERISTICS:
        (A) LENGTH: 208
        (B) TYPE: amino acid
        (D) TOPOLOGY: linear     (ii) MOLECULE TYPE: protein     (xi) SEQUENCE DESCRIPTION: SEQ ID NO:2:

```
Met Ala Thr Phe Gln Gly Thr Gln Gln Lys Cys Asn Ala Cys Asn Lys
 1               5                  10                  15

Thr Val Tyr Leu Val Asp Lys Leu Thr Ala Asp Asn Arg Val Phe His
             20                  25                  30

Lys Ala Cys Phe Arg Cys His His Cys Lys Gly Thr Leu Lys Leu Ser
         35                  40                  45

Asn Tyr Asn Ser Phe Glu Gly Val Leu Tyr Cys Arg Pro His Tyr Asp
     50                  55                  60

Gln Leu Phe Lys Arg Thr Gly Ser Leu Asp Lys Ser Phe Glu Gly Thr
 65                  70                  75                  80

Pro Lys Val Val Lys Pro Glu Arg Gln Ile Asp Ser Glu Ser Ala Leu
                 85                  90                  95

Lys Val Met Asn Ser Phe Gly Gly Thr Arg Glu Lys Cys Ala Ala Cys
            100                 105                 110

Ser Lys Thr Ala Tyr Pro Ile Glu Arg Val Thr Val Asn Gly Thr Ile
        115                 120                 125

Tyr His Lys Ser Cys Phe Lys Cys Thr His Gly Gly Cys Thr Ile Ser
    130                 135                 140

Pro Ser Asn Tyr Ile Ala His Glu Gly Lys Leu Tyr Cys Lys His His
145                 150                 155                 160

His Ile Gln Leu Phe Lys Glu Lys Gly Asn Tyr Ser Gln Leu Glu Thr
                165                 170                 175

Glu Arg Glu Lys Gln Ala Ala Thr Ala Ala Asn Lys Val Pro Ala Pro
            180                 185                 190

Ala Ala Thr Ser Thr Thr Thr Thr Thr Glu Ile Ala Ala Glu Ser
        195                 200                 205
```

(2) INFORMATION FOR SEQ ID NO:3:

(i) SEQUENCE CHARACTERISTICS:
        (A) LENGTH: 50
        (B) TYPE: nucleic acid
        (C) STRANDEDNESS: single
        (D) TOPOLOGY: linear (ii) MOLECULE TYPE: other nucleic acid
             (A) DESCRIPTION: /desc="synthetic DNA"

(xi) SEQUENCE DESCRIPTION: SEQ ID NO:3:

GAGAGAGAGA GAGAGAGAGA ACTAGTCTCG AGTTTTTTTT TTTTTTTTTT                50

(2) INFORMATION FOR SEQ ID NO:4:

(i) SEQUENCE CHARACTERISTICS:
             (A) LENGTH: 13
             (B) TYPE: nucleic acid
             (C) STRANDEDNESS: single
             (D) TOPOLOGY: linear (ii) MOLECULE TYPE: other nucleic acid
             (A) DESCRIPTION: /desc="synthetic DNA"

(xi) SEQUENCE DESCRIPTION: SEQ ID NO:4:

AATTCGGCAC GAG                                                        13

(2) INFORMATION FOR SEQ ID NO:5:

(i) SEQUENCE CHARACTERISTICS:
             (A) LENGTH: 9
             (B) TYPE: nucleic acid
             (C) STRANDEDNESS: single
             (D) TOPOLOGY: linear (ii) MOLECULE TYPE: other nucleic acid
             (A) DESCRIPTION: /desc="synthetic DNA"

(xi) SEQUENCE DESCRIPTION: SEQ ID NO:5:

CTCGTGCCG                                                              9

(2) INFORMATION FOR SEQ ID NO:6:

(i) SEQUENCE CHARACTERISTICS:
             (A) LENGTH: 219
             (B) TYPE: amino acid
             (D) TOPOLOGY: linear (ii) MOLECULE TYPE: protein (xi) SEQUENCE DESCRIPTION: SEQ ID NO:6:

Met Lys Ser Phe Thr Gly Thr Thr Gln Lys Cys Thr Val Cys Glu Lys
 1               5                  10                  15

Thr Val Tyr Leu Val Asp Lys Leu Val Ala Asn Gln Arg Val Tyr His
                20                  25                  30

Lys Ala Cys Phe Arg Cys His His Cys Asn Ser Thr Leu Lys Leu Ser
            35                  40                  45

Asn Phe Asn Ser Phe Asp Gly Val Val Tyr Cys Arg His His Phe Asp
        50                  55                  60

Gln Leu Phe Lys Arg Thr Gly Ser Leu Glu Lys Ser Phe Asp Gly Thr
 65                  70                  75                  80

Pro Lys Phe Lys Pro Glu Arg Thr Phe Ser Gln Glu Thr Gln Ser Ala
                85                  90                  95

Asn Arg Leu Ser Ser Phe Phe Glu Gly Thr Arg Asp Lys Cys Asn Ala
            100                 105                 110

Cys Ala Lys Ile Val Tyr Pro Ile Glu Arg Val Lys Val Asp Gly Thr
        115                 120                 125

Ala Tyr His Arg Ala Cys Phe Lys Cys Cys His Gly Gly Cys Thr Ile
    130                 135                 140

-continued

```
Ser Pro Ser Asn Tyr Ile Ala His Glu Gly Arg Leu Tyr Cys Lys His
145                 150                 155                 160

His His Ile Gln Leu Phe Lys Lys Glu Gly Asn Tyr Ser Gln Leu Glu
            165                 170                 175

Val Glu Glu Thr Val Ala Ala Pro Ala Glu Ser Glu Thr Gln Asn Thr
            180             185                 190

Glu Thr Gln Asn Ala Glu Thr Gln Asn Ala Asp Thr Gln Asn Ala Asp
        195                 200                 205

Thr Gln Asn Thr Glu Thr Gln Asn Gly Ser Val
    210                 215
```